United States Patent
Shedd et al.

(10) Patent No.: US 6,393,899 B1
(45) Date of Patent: May 28, 2002

(54) APPARATUS AND METHOD FOR AUTOMATED BIOMONITORING OF WATER QUALITY

(75) Inventors: Tommy Ray Shedd, Middletown, MD (US); Mark Wesley Widder, Chambersburg, PA (US); Jeffrey Daniel Leach, Frederick, MD (US); William Hendrik Van Der Schalie, Walkersville, MD (US); Robert Charles Bishoff, Boonsboro, MD (US)

(73) Assignee: Geo-Centers, Inc., Newton Centre, MA (US); a part interest ( * ) Notice: Subject to any disclaimer, the term of this patent is extended or adjusted under 35 U.S.C. 154(b) by 0 days.

(21) Appl. No.: 09/492,104

(22) Filed: Jan. 27, 2000

Related U.S. Application Data

(63) Continuation-in-part of application No. 09/039,314, filed on Mar. 16, 1998, now Pat. No. 6,058,763.
(60) Provisional application No. 60/041,533, filed on Mar. 17, 1997.

(51) Int. Cl.[7] .......................... G01N 33/00; A01K 63/00
(52) U.S. Cl. ...................................... 73/61.41; 119/224
(58) Field of Search ..................... 73/61.41; 119/224, 119/238, 239, 240

(56) References Cited

U.S. PATENT DOCUMENTS

| | | | |
|---|---|---|---|
| 4,626,992 A | * | 12/1986 | Greaves et al. |
| 5,140,855 A | | 8/1992 | Gruber |
| 5,307,052 A | * | 4/1994 | Harrison et al. |
| 5,469,144 A | * | 11/1995 | Gradzki et al. |
| 5,804,705 A | * | 9/1998 | Florion et al. .............. 73/61.41 |
| 6,058,763 A | * | 5/2000 | Shedd et al. |
| 6,119,630 A | * | 9/2000 | Lobsiger et al. ............ 119/238 |

FOREIGN PATENT DOCUMENTS

| | | | |
|---|---|---|---|
| GB | 2 195 543 | * | 4/1988 |
| WO | WO 95/14925 | * | 6/1995 |

OTHER PUBLICATIONS

Nelms et al, "BeRM: Bioelectric Response Monitor", proceedings from IEEE SouthEast Con '92, Apr. 12–15, 1992, Birmingham, Alabama, IEEE, vol. 1, No. 12, pp. 91–94 (1992).*

(List continued on next page.)

*Primary Examiner*—Hezron Williams
*Assistant Examiner*—Jay L. Politzer
(74) *Attorney, Agent, or Firm*—Oblon, Spivak, McClelland, Maier & Neustadt, P.C.

(57) ABSTRACT

An automated biomonitoring system for monitoring water quality includes an exposure chamber for housing an aquatic organism having ventilatory behavior and body movement sensitive to water quality. Electrodes capture electrical signals produced by the organism during its ventilatory behavior and body movement, and a controller responsive to signals from the electrodes determines one or more ventilatory parameters based on the signals. The ventilatory parameters are compared with corresponding thresholds to determine when the water to which the organism is exposed has caused physiological stress to the organism. The signals captured by the electrodes may be corrected for variations in water conductivity so that the signals processed by the controlled are not influenced by conductivity.

12 Claims, 10 Drawing Sheets

OTHER PUBLICATIONS

Notification of Transmittal of the International Search Report or the Declaration issued on Jul. 15, 1998, in corresponding PCT/US98/04870.*

ASTM Standard Guide for Ventilatory Behavorial Toxicology Testing of Freshwater Fish, E1768–95, 9, ASTM, West Conshohocker, PA.*

Shedd, T.R. et al, "Evaluation of an Automated Fish Ventilatory Monitoring System in a Short–Term Screening Test for Chronic Toxicity," U.S. Army Biomedical Research and Development Laboratory. Technical Report AD A172116, Fort Detrick, MD 1986.*

Continuous Automated Biomonitoring: Perspectives and Applications, U.S. Army Corps of Engineers Seventh Innovative Technology Transfer Workshop (Mar. 20, 1997).

W. H. Van Der Shalie, in *Aquatic Toxicolgy: Third Conference ASTM STP 707*; J. Eaton, P. Parrish, and A. Hendricks (eds.), Philadelphia, PA. pp. 233–242 (1980).

W.H. Van Der Shalie et al., in *Automated Biomonitoring*; D. Gruber and J. Diamond (eds.), Horwood Publishers, West Sussex, England, pp. 67–74 (1988).

D. Gruber, et al., *Journal of Water Pollution Control Federation*, vol. 51, pp. 2744–2751 (Nov. 1979).

G. F. Westlake, et al., in *ASTM STP 607*, J. Cairns, Jr., K. L. Dickson, and G.F. Westlake, (eds.), pp. 30–37 (1997).

R. W. Carison, et al., *Water Research*, vol. 12, pp. 1–6 (1978).

* cited by examiner

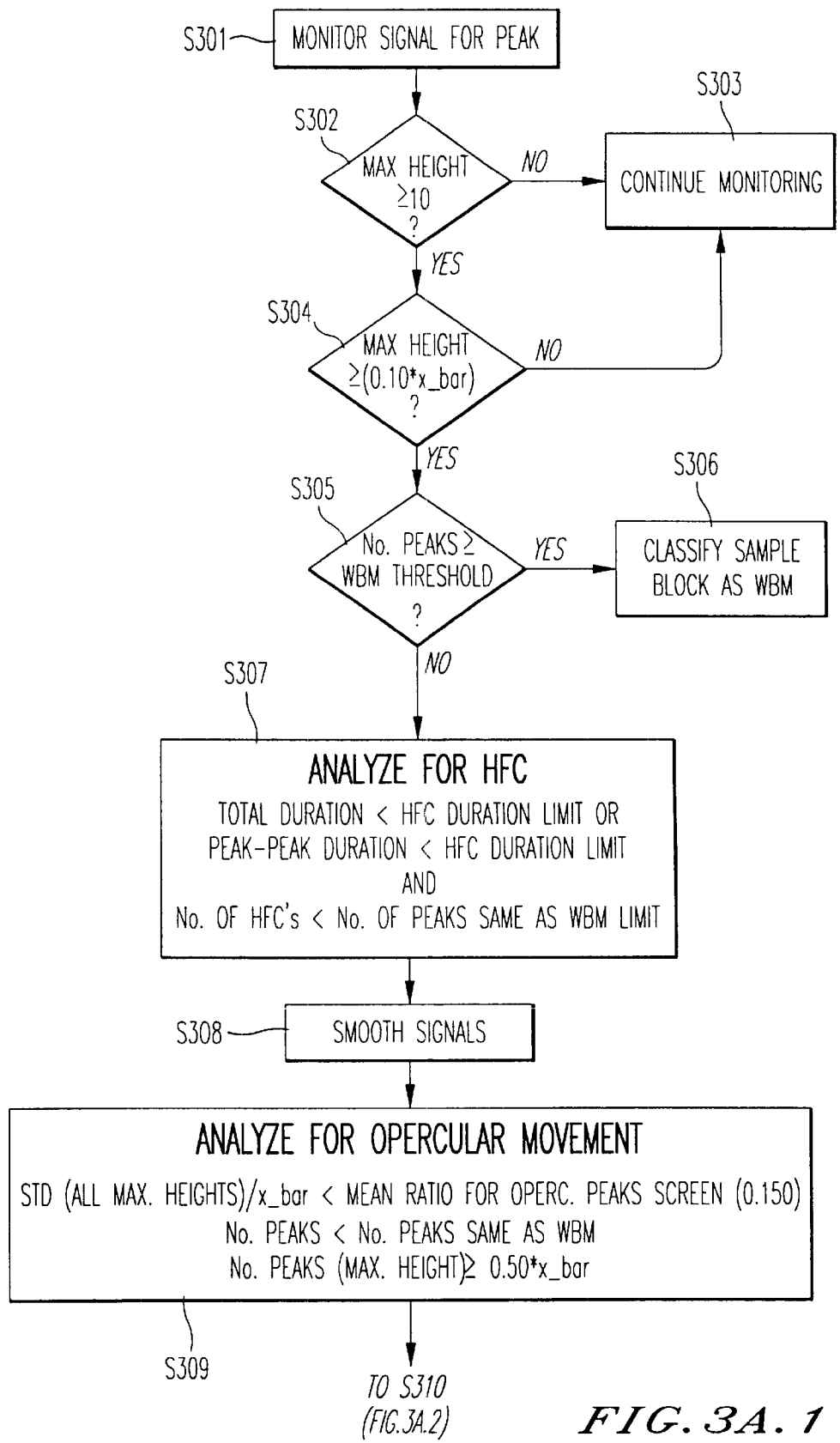
FIG. 3A.1

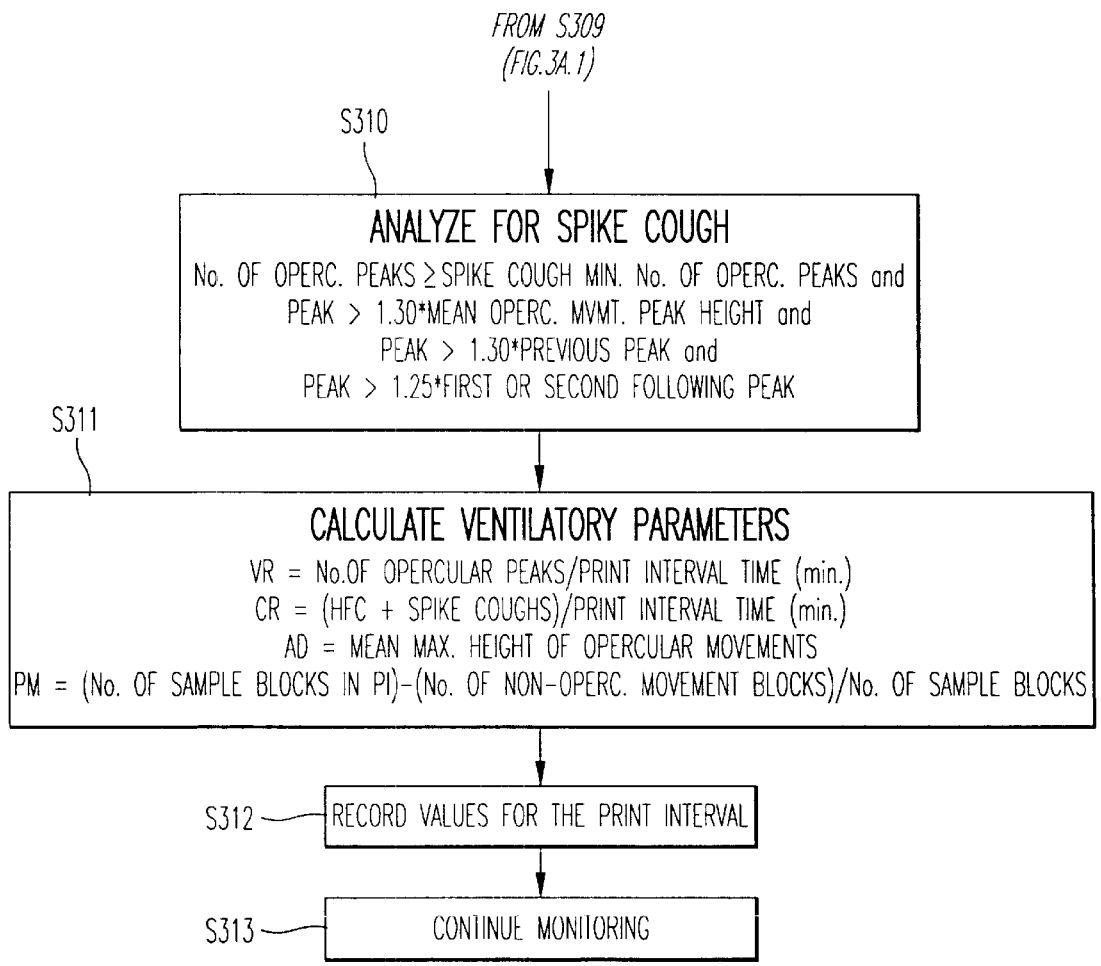
FIG. 3A.2

APPARATUS AND METHOD FOR AUTOMATED BIOMONITORING OF WATER QUALITY

REFERENCE TO RELATED APPLICATIONS

This application is a continuation-in-part of U.S. patent application Ser. No. 09/039,314, filed on Mar. 16, 1998 now U.S Pat. No. 6,058,763, the disclosure of which is incorporated by reference, which claims the benefit of U.S. Provisional Application No. 60/041,533, filed on Mar. 17, 1997.

GOVERNMENT LICENSE RIGHTS

The U.S. Government has a paid-up license in this invention and the right in limited circumstances to require the patent owner to license others on reasonable terms as provided for by the terms of contract No. DAMD17-93-C-3006 awarded by the U.S. Army.

BACKGROUND OF THE INVENTION

1. Field of the Invention

The present invention relates generally to an apparatus and method for monitoring water quality. More particularly, the present invention relates to an apparatus and method for monitoring water quality using the ventilatory behavior and body movement of aquatic organisms.

2. Description of the Related Art

Ventilatory responses are often some of the first prelethal symptoms exhibited by animals to environmental stressors. Continued, abnormal ventilatory behavior, such as rapid, shallow, or erratic breathing, can indicate physiological damage that may be irreversible. Changes in the ventilatory behavior of fish have been shown to be a reliable indicator of accidental toxic spills or "slugs" of pollutants in wastewater and drinking water systems. Accordingly, ventilatory biomonitoring systems can serve as an early indicator of impending damage to aquatic ecosystems and possible harm to humans.

The technological means are readily available to log and display ventilatory signals for subsequent analysis. As a result, there are a considerable number of studies that have examined ventilatory behavior of fish and other aquatic organisms. A large number of substances at lethal levels have been shown to elicit ventilatory responses relatively quickly. For many pollutants, a significant response was often generated in less than one hour of exposure to concentrations approaching the 96-hour LC50 (the concentration at which fifty percent of the organisms expire within 96 hours of exposure). Studies performed using subacutely toxic samples of effluents or individual pollutants (concentrations well below the reported LC50 concentration) often documented responses within one to ten hours of exposure.

Although a variety of organisms have been examined for this purpose, including crayfish, aquatic insect larvae, and bivalves, most research in aquatic ventilatory behavior has used freshwater fish species. This is largely because fish are generally more ecologically "visible" in their importance in aquatic systems and many species (particularly the salmonids and centrarchids) have large opercular flaps that yield relatively clear ventilatory signals for measurement and evaluation.

The ventilatory parameters in fish that have been shown to be affected by toxicity include ventilatory rate (opercular movement over time), depth of ventilation (amplitude), coughing or gill purge rate, and erratic episode frequency due to sudden movement of the organism. Most commonly, changes in just ventilatory rate, as opposed to the other parameters just mentioned, have been used as a bioindicator of toxic conditions. The depth of ventilation and gill purge or cough rate, however, have been reported to be more sensitive indicators of toxicity for some compounds.

Changes in ventilatory rate are often determined by manual examination of the peaks per unit area on a strip-chart recording. Depth of ventilation or signal amplitude is similarly measured from top to bottom of the waveform on the strip chart. Cough rate has been more difficult to determine even with manual examination of a strip chart as several different types of coughs may be present, each with its own characteristic waveform pattern. Also, without the use of simultaneous video techniques, the actual occurrence of a cough is not always clear.

SUMMARY OF THE INVENTION

Accordingly, one object of the present invention is to provide an apparatus for automated biomonitoring of water quality.

Another object of the present invention is to be able to include behavioral parameters such as the depth of ventilation, cough rate, and whole body movement of an aquatic organism in addition to ventilatory frequency data in the automated biomonitoring of water quality.

A related object of the present invention is to be able to further include water quality characteristics such as dissolved oxygen, pH, temperature, and conductivity in the biomonitoring of water quality.

Another object of the present invention is to provide improved waveform processing of data signals from aquatic organisms to reduce spurious data signals.

Another object of the present invention is to be able to provide an array of biomonitor exposure chambers with an integral water delivery and drain system for improved ventilatory signal data collection and biomonitor operation.

Another object of the present invention is to be able to provide a programmable alarm response that includes automated water sampling and optional remedial action such as isolation of the water pollution source.

These and other objects will be apparent from the following description.

According to one aspect of the invention, an apparatus for monitoring and evaluating water quality includes an exposure chamber for housing an aquatic organism and containing water to be monitored, and electrodes for sensing electrical signals generated by the organism during ventilatory behavior and body movement in the water being monitored. Electrical signals picked up by the electrodes are supplied to an automatic controller, which determines one or more ventilatory and body movement parameters based on the signals from the electrodes. The controller compares the parameters with corresponding thresholds to determine when the water to which the organism is exposed has caused physiological stress to the organism.

The controller may determine a wide variety of ventilatory and body movement parameters. In a preferred embodiment, the controller determines at least the ventilatory frequency, the average ventilatory depth, and the cough rate of the organism.

In one embodiment, signals received from the electrodes may be corrected to compensate for the effect of the conductivity of the water on signal amplitude.

The system may further include various devices operative in response to a determination of a water quality problem by the controller. For example, it may include an alarm mechanism which generates an alarm, a sample device which collects samples of the water being monitored for subsequent analysis, or a diverting mechanism for diverting the water being monitored to a storage tank and preventing the water from being discharged into the environment.

According to another aspect of the present invention, a method of evaluating water quality comprises measuring electrical signals generated by an aquatic organism disposed in water to be monitored, determining one or more ventilatory and body movement parameters of the organism based on the signals, and comparing the parameters with corresponding thresholds to determine when the water to which the organism is exposed has caused physiological stress to the organism.

The monitoring and determination of ventilatory and body movement parameters of an aquatic organism by an automated controller as taught in the present invention provides for continuous, around-the-clock monitoring of water quality with fast signal processing and good reproducibility of results, which are otherwise not possible with manual methods of biomonitoring. The present invention can employ a plurality of ventilatory and body movement parameters to provide greater detection sensitivity and accuracy over systems using a one-parameter analysis, and the present invention is readily integrated with effluent control systems for wastewater treatment plants, factories, and other possible sources of pollutants. The invention also may be used to monitor and evaluate the quality of a body of water such as a lake or stream, or the inlet to a potable water treatment facility, providing a detection capability of inadvertent or intentional toxic contamination of the water source. Such contamination could otherwise go undetected without the present invention until human health is effected and traced to the source of contaminated drinking water. In addition, the exposure chamber of the present invention provides improved biomonitoring of aquatic organisms with a top-bottom electrode arrangement, uniform mixing of the water prior to organism exposure, and reduced water stratification within the chamber.

DESCRIPTION OF PREFERRED EMBODIMENTS

Figure 1:
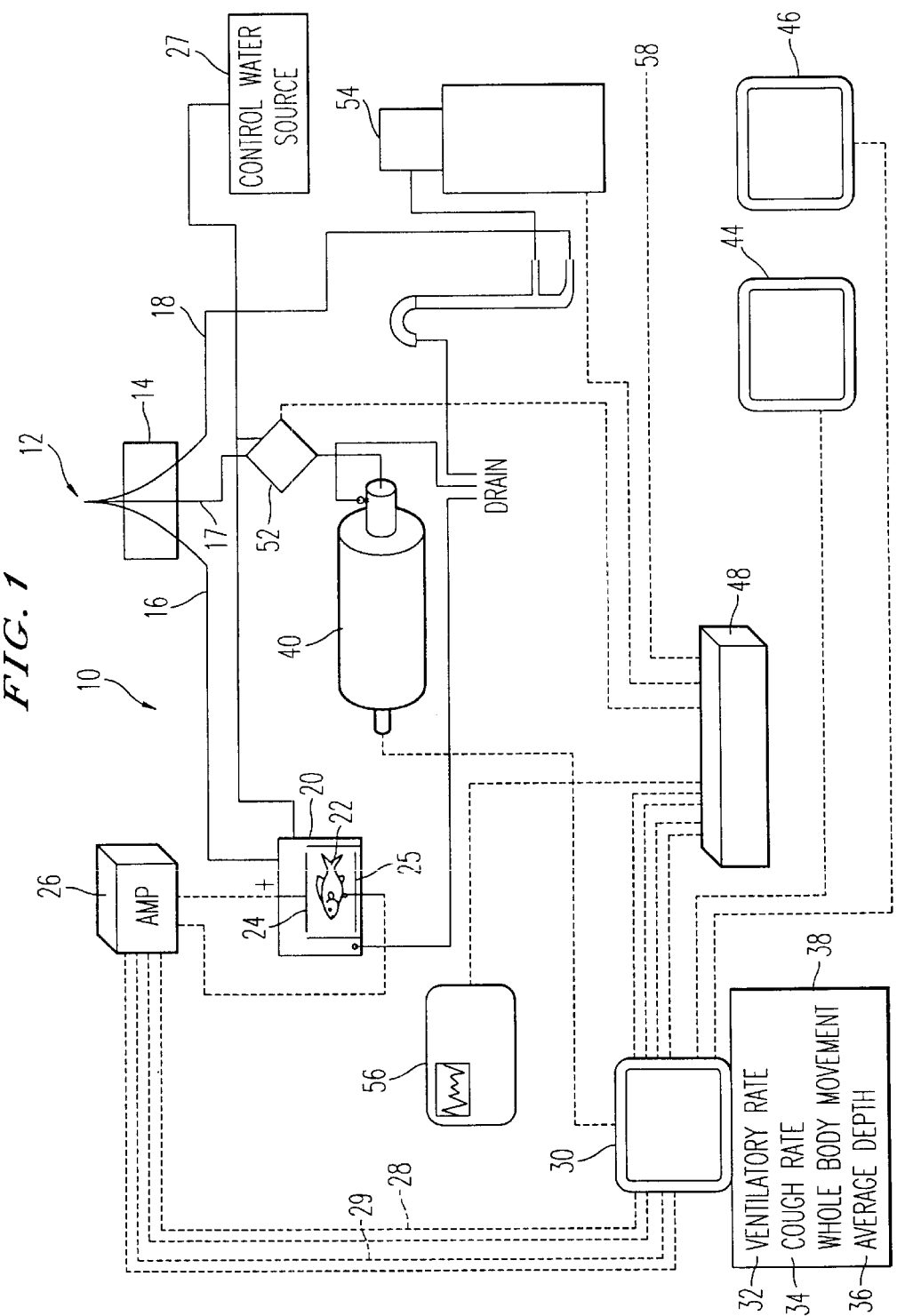
FIG. 1 is a schematic of an embodiment of an automated biomonitoring system according to the present invention.

FIG. 1 illustrates an embodiment of an automated biomonitoring system 10 in accordance with the present invention. An inlet stream of sample water flows from source 12 to water meter 14 where the inlet water stream is divided into three outlet streams 16–18. The water source 12 to be monitored and analyzed by the present invention may be any source of water. Water sources to be monitored include, but are not limited to, naturally occurring water sources such as lakes, rivers, streams, and harbors, and other natural bodies of water. The water source 12 to be monitored may also come from a source of drinking water as it is supplied to the inlet of a potable water treatment facility, or source 12 may be taken from a possible pollution source such as the discharge from a facility for treating wastewater or groundwater before the water is discharged from the treatment facility. As illustrated in the following discussion, system 10 provides a general-purpose automated biomonitoring system for use in monitoring the water quality of any source of water, and is readily integrated with other control systems or data monitoring devices.

Returning to FIG. 1, water from source 12 flows to one or more exposure chambers 20 each containing one or more fish 22 via outlet stream 16. Fish physiological signals are captured by electrodes 24–25, and transmitted to amplifier 26 where the electrical signals are filtered and amplified. Although only one channel corresponding to one fish is illustrated here, the system may include any number of channels. For example, the preferred embodiment contains four exposure chambers, each having eight fish compartments, and a 32-channel amplifier for simultaneous monitoring of up to thirty-two fish. In this way, one group of fish can be exposed to water sampling source 12 while another fish group is exposed to control water 27 and still another fish group is being acclimated or monitored for benchmark data prior to exposure. Eight fish exposed to the same water provide a statistically significant sample group of organisms to determine whether physiological stress has occurred due to the water quality as opposed to illness in, or injury to, an individual fish that was caused by something other than water quality. Four sets of eight fish are used to provide the control and exposure groups as described above.

The signals picked up by the electrodes, which will be referred to as ventilatory signals, are in analog form. The terms "ventilatory signal" and "ventilatory parameter" as used in this invention include data representative of body movement other than the movement of opercular flaps. Such non-opercular movement could, for example, include data resulting from an erratic episode due to sudden movement of the aquatic organism 22 within exposure chamber 20. The analog ventilatory signals picked up by electrodes 24–25 are provided from amplifier 26 to a controller 30 via signal cables 28–29. As fully described below, controller 30 is used to convert the analog electrical signals to digital signals, to further amplify and filter the signals, and to perform an analysis to determine ventilatory and body movement parameters, such as ventilatory rate 32, cough rate 34, average depth 36, and percent whole body movement 38. These parameters are continuously monitored and compared to previously measured data, control fish data, or both to determine the present physiological stress level of exposure fish 22. Water analysis data from a water quality sensor 40 also are monitored and analyzed using controller 30. These data typically include the dissolved oxygen level, temperature, pH, and conductivity of the sample water stream 17 from source 12, which are monitored and compared to preset alarm limits, and may be correlated with the measured physiological responses.

A regression analysis, for example, may be performed by controller 30 to adjust the measured ventilatory parameters for changes in dissolved oxygen level and temperature as described in detail below. Water characteristic data from sensor 40 also may be used to corroborate the ventilatory parameter analysis by controller 30. A marked change in pH level. for example, may strengthen a determination of elevated physiological stress evidenced by a change in ventilatory rate 32. On the other hand, further evaluation is indicated where modest changes in ventilatory behavior are detected in the absence of any measurable change in dissolved oxygen level, temperature, pH, and conductivity of the sample water stream 17.

A sampler 54 is provided for automated water sampling and further off-line analysis of the water quality. A control signal from controller 30 to sampler 54 via termination panel 48 will result in a sample being taken from water stream 18. This sample is stored and refrigerated in sampler 54 for preservation and subsequent analysis with standard analytical chemistry equipment or other means. As this sampling is performed automatically by sampler 54 in response to a control signal from automated controller 30, the resulting samples may serve as valuable physical evidence of the specific water content at a given moment and locale.

Signal data from controller 30 may be provided to various components such as a remote host 44, a remote monitor 46, and a termination panel 48. Termination panel 48 can be used to provide control signals to components such as a solenoid valve 52 and the sampler 54. Termination panel 48 also can provide output signals to an oscilloscope 56 and a control signal 58. Oscilloscope 56 provides manual signal conditioning and analysis without changing parameters or interfering with the process function of controller 30.

Optional remote monitor 46 provides a display of the signals as processed by controller 30 for viewing at another location, such as an effluent treatment facility upstream of source 12. Optional remote host 44 provides the ability to change the parameters and functions of controller 30 in addition to monitoring and recording signals from controller 30. Host 44 also may be used to perform programmable response functions to take remedial action in response to the information provided by automated biomonitoring system 10. Remote host 44 may be used, for example, to control an effluent water treatment process. Control of the water treatment process can thus include aquatic organism physiological stress data along with other parameters, providing real-time information on measurable biological and ecological effects of the particular water being discharged. Controller 30 also provides a control signal 58 via termination panel 48 in response to an out-of-limit condition. This control signal can be used to sound an alarm or to divert effluent water to a holding tank, for example, without the use of another microprocessor or control system.

Having provided a general description of the automated biomonitoring system 10, attention is now turned to a general description of its operation.

In this application, the physiological stress to bluegills (*Lepomis macrochirus*), characterized by changes in fish ventilation and movement patterns, is used as an early warning to identify developing acute toxicity of a treated groundwater discharge or effluent from a wastewater treatment facility.

A wide variety of other test organisms are also available for use with the present invention, including but not being limited to rainbow trout (*Oncorhynchus mykiss*), pink salmon (*Oncorhynchus gorbuscha*), crayfish (Orconectes sp.), and any other species appropriate for examining water pollutant effects. Juvenile bluegill are often the preferred choice as the species are widely available, are easily maintained over a wide range of temperature and pH levels, are relatively sensitive to a number of pollutants, and have large opercular flaps which elicit a strong ventilatory signal. Regardless of the choice of test organism, it is desirable to acclimate the organism to the experimental conditions prior to exposure and data collection.

A typical operation begins with a plurality of fish, such as sixteen fish, held in control water for a three-day acclimation period followed by four days of baseline data collection. This may be performed using two exposure chambers 20, each housing one group of fish. One of the exposure chambers 20, containing some of the fish (such as eight fish) is then placed in effluent water with the second set of fish (such as the other eight fish) remaining in control water. In the subsequent monitoring, system 10 provides immediate analysis of statistically significant departures from baseline conditions for fish in both the control and effluent-exposed groups. After a suitable period of exposure to effluent (such as two weeks), new fish are placed on-line to continue monitoring of the effluent. As a general procedure, fish feeding during testing should be avoided as feeding activity causes interference with ventilatory signal analysis.

When system 10 identifies a potentially toxic effluent as described fully below, a water sample may be automatically collected using sampler 54 for off-line chemical analysis. The remote monitor 46, which may be located in the treatment facility or factory control room, provides an early warning that the discharge water is inducing physiological stress to aquatic organisms and, if continued, may produce harmful effects to the environment and possible danger to human health. By providing an early warning to facility operators, remedial action can be taken quickly to avoid harmful effects. The water collected by sampler 54 can be used to further analyze the content of the suspect water and as physical evidence of water conditions at a particular time. As desired by the user of system 10, the toxic effluent may be automatically diverted by control signal 58 to storage tanks until the cause of the toxic effluent is isolated and corrected. Corrective action may, for example, require plant operators to adjust certain parameters used in the treatment of the plant water before releasing it into the discharge stream monitored by system 10. For example, corrective action may call for increasing the duration that the plant water is held in treatment tanks, reactors, neutralizing beds, and the like before allowing the water to be discharged to the environment.

In the above example, system 10 was used as an automated early warning system to identify developing acute toxicity of a treated groundwater discharge from a wastewater treatment facility. The system 10 also may be integrated with other sources of discharge water, such as a sewer treatment plant, an industrial plant, or factory for providing the same type of automated early warning and corrective action as described above. The present invention also may be used to monitor a body of water, such as a lake, bay, river, or stream, including a source of drinking water, for changes in water quality. When used to monitor the inlet to a potable water treatment facility, for example, system 10 provides an automated early warning of an inadvertent or intentional contamination of the potable water supply that may otherwise go unnoticed until human heath effects are detected and traced to the source of contaminated drinking water. This application would use the same basic acclimation, baseline, and monitoring procedures as described in the above example with the same basic system components. An alarm signal in response to an identification of contaminated water by controller 30, can be provided to the appropriate health officials upon immediate detection of a possible danger.

Having provided a general description of components and operation of the present invention, attention is now turned to a detailed description of the signal processing steps performed by the system 10 to measure and analyze aquatic organism response. As mentioned above, the key physiological stress indicators used in the present invention are ventilatory rate 32, cough rate 34, average depth 36, and percent whole body movement 38. The following discussion defines the terms and mathematical operations used in this analysis.

Figure 2:
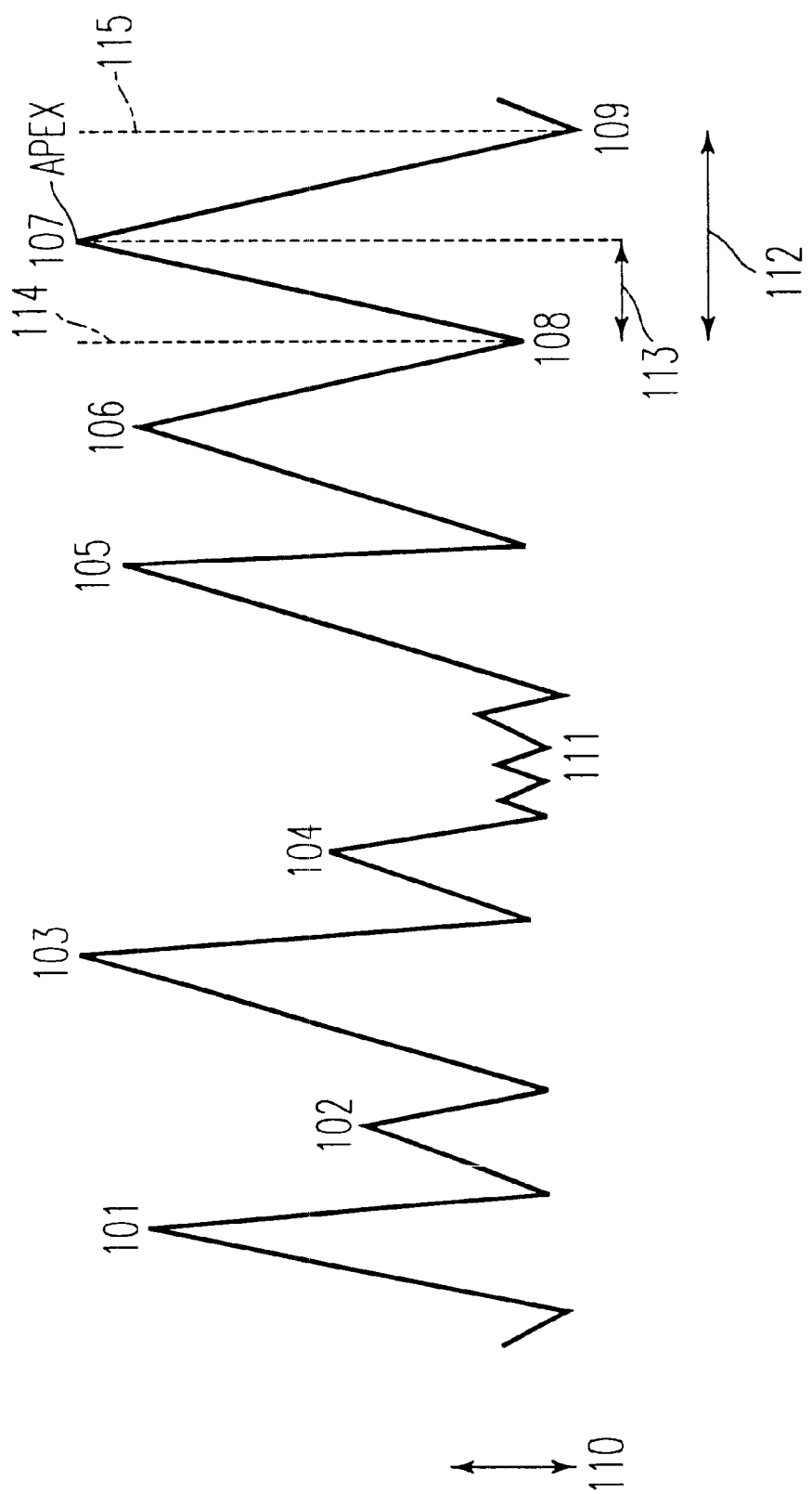
FIG. 2 is a representative signal sample illustrating ventilatory signal analysis in accordance with this invention.

Turning to FIG. 2 and FIG. 3, a representative signal sample and flowchart are illustrated to describe the ventilatory signal analysis performed by controller 30 in accordance with the present invention. In the following example, a twelve-bit analog-to-digital converter is used to convert the analog minus-ten to plus-ten volt signal from amplifier 26 to a digital 0 to 4095 integer value. The number of bits, analog scale, and digital scale used, however, may be varied as desired while still performing the following analysis in accordance with the present invention.

As illustrated in FIG. 2, a ventilatory signal includes a series of peaks 101–107 and troughs 108–109. Time is illustrated from left to right, with the most recent signal appearing on the far right of FIG. 2 near trough 109. Peak parameters used in this level one analysis include total duration, rear duration, peak-to-peak duration, apex, rear height, minimum height, and maximum height. A peak is defined as a signal maximum point (apex) where the difference between the value of the signal at the peak and the value of the signal at the immediately preceding or following trough is greater than a specified threshold 110. Step S301 in FIG. 3A begins signal monitoring for the next peak. The peak picking threshold 110 is generally never less than ten as measured on the 0 to 4095 integer scale, but may be adjusted upward based upon the mean maximum peak height x_bar for the previous print interval as described below. Step S302 determines whether the maximum height is greater than or equal to 10, and step S304 determines whether the same value is greater than or equal to ten percent of x_bar. If both conditions S302 and S304 are met, then the value is identified as a peak. If either one of these conditions is not met, or if both conditions are not met, then monitoring for the next peak is continued in step S303. In this way, low amplitude signals 111, which do not exceed the minimum threshold 110 are not labeled as peaks.

The mean maximum height used in step S304 is based upon data obtained in the previous print interval. A print interval is defined as a specified number of contiguous sample blocks that are analyzed and presented together in the present invention, while a sample block is defined as the ventilatory signal versus time, as illustrated in FIG. 2, over a specified duration. The print interval is normally set to fifteen minutes with sample block duration of fifteen seconds, but other values may be selected based upon user preference. The mean maximum height for the sample block is used in some cases, while the mean maximum height for the print interval is used in others. The following discussion specifies which value of x_bar is being used for a particular step in the process of FIG. 3.

Returning to FIG. 2, troughs such as 108 and 109 are defined as a signal minimum point between peaks. Total duration 112 is the time between consecutive troughs, whereas rear duration 113 is the time between a peak and the preceding trough. Rear height 114 is the difference in the absolute value of amplitude between peak value and the preceding trough value. Forward height 115 is the difference between peak value and the succeeding trough value. The minimum peak height is defined as the lesser of the rear height and forward height values, while the maximum peak height is defined as the greater of the two values.

Step S305 determines if the number of peaks in a sample block is greater than a specified whole body movement threshold, generally taken as forty-eight peaks. Again, another value may be selected for the whole body movement threshold based upon user preference. If the condition of step S305 is true, then step S306 classifies the entire sample block as whole body movement as opposed to ventilatory behavior. If the number of peaks in a sample block is less than the whole body movement threshold, then processing continues in step S307. At this point of signal analysis, the ventilatory frequency could be calculated as the number of opercular peaks thus identified in steps S304 and S305 divided by the print interval time in minutes. The present invention, however, goes beyond this first level analysis to analyze for high frequency coughs and spike coughs. As discussed in the steps below, the signal is smoothed after identifying high frequency coughs and before determining ventilatory frequency. This provides for improved data analysis in determining ventilatory parameters. In addition, the locations of the high frequency cough peaks are tagged so as not to double count these HFC-identified peaks as spike coughs.

Step S307 identifies high frequency coughs in a level two analysis as follows. If either the total duration or the peak-to-peak duration is less than the high frequency cough duration limit, then the peak is identified as a high frequency cough provided that the peaks in a peak-to-peak evaluation or the troughs in a trough-to-trough evaluation are outside of the noise band limits. Step 307 then determines whether the number of high frequency coughs is greater than or equal to the threshold for whole body movement. If so, the entire sample block is considered whole body movement as opposed to high frequency coughs or other ventilatory behavior. A time of 0.193 seconds has been used as the high frequency cough duration limit in step S307. Integer values 2108 for peaks and 1988 for troughs have been used as the initial noise band limits. After the first print interval, the mean maximum height for the print interval x_bar is calculated, and the noise band is adjusted by setting the upper limit equal to the corresponding integer equivalent of x_bar multiplied by 0.15, and the lower limit equal to the corresponding integer equivalent of x_bar multiplied by −0.15. These new noise limits are used in subsequent step S307 analyses for high frequency coughs. Again, the initial and adjusted noise level bands may be specified differently based upon user preference.

Step S308 smooths the signal sample to remove the high frequency coughs from the data for subsequent analysis, and tags the locations of the high frequency cough peaks so as not to double count these HFC-peaks as spike coughs. The smoothing function is performed using a standard curve-smoothing algorithm, such as a low-pass digital filter, while the tagging is performed with a simple binary array of true/false data. The algorithm selected for the smoothing function should remove the high frequency coughs while preserving the remaining ventilatory data for further analysis. Step S308 provides improved data analysis in steps S309–S311 by removing the high frequency coughs from the sample data having been already analyzed for high frequency coughs in step S307. The resulting data are more amenable to opercular movement analysis and spike cough determination with the HFC peaks removed.

Step S309 performs an opercular movement analysis as follows. The ratio of the standard deviation of all maximum heights to mean maximum height of the sample block x_bar is calculated and compared with the opercular peak threshold, which is generally taken as 0.15. If less than the threshold, then all non-HFC peaks in the sample block are considered opercular movements. If the ratio is greater than or equal to the threshold, then the number of peaks with a total duration less than the whole body movement limit of 0.36 seconds is determined. If this number of peaks is greater than the whole body movement threshold of six peaks, then the sample block is considered whole body movement. If not, then the number of peaks with a maximum height greater than or equal to fifty percent of the sample block mean maximum height x_bar is the number of opercular movements. Once again, other values for peak threshold, whole body duration, and the like may be specified for use in step S309 depending on user preference.

Step S310 performs a spike cough analysis on the non-HFC peaks as follows. A given peak is considered a spike cough when the following four conditions are met. First, the number of opercular peaks in the sample block is greater than or equal to the spike cough threshold, which is generally taken as seven peaks. Second, the peak value is greater than 1.3 times the mean maximum height x_bar for the sample block. Third, the peak value is greater than 1.3 times the previous peak. Fourth, the peak value is greater than 1.25 times the first or second following peak. Again, these threshold factors may be altered from the above values depending on user preference.

Having performed the higher level analysis of steps S307–S310, ventilatory parameters are then calculated as follows. Step S311 calculates the ventilatory rate, cough rate, average depth, and percent whole body movement. Ventilatory rate (VR) is calculated in step S311 as the number of opercular peaks during a given print interval, divided by the time in minutes of the print interval. Cough rate (CR) is calculated as the sum of the high frequency coughs and spike coughs divided by the print interval time in minutes. Average depth (AD) is calculated as the mean maximum height of all opercular movement peaks during a print interval. This is the same value as mean maximum height of the print interval x_bar used in the above analysis. Percent whole body movement (PM) is the number of sample blocks in the print interval less the number of non-opercular movement blocks in the print interval divided by the total number of sample blocks in the print interval. This value may be multiplied by 100 and expressed as a percentage. Step S312 records the values of VR, CR, AD, and PM, as calculated in step S311 for subsequent use, while step S313 continues monitoring of the ventilatory signal.

Figure 3B:
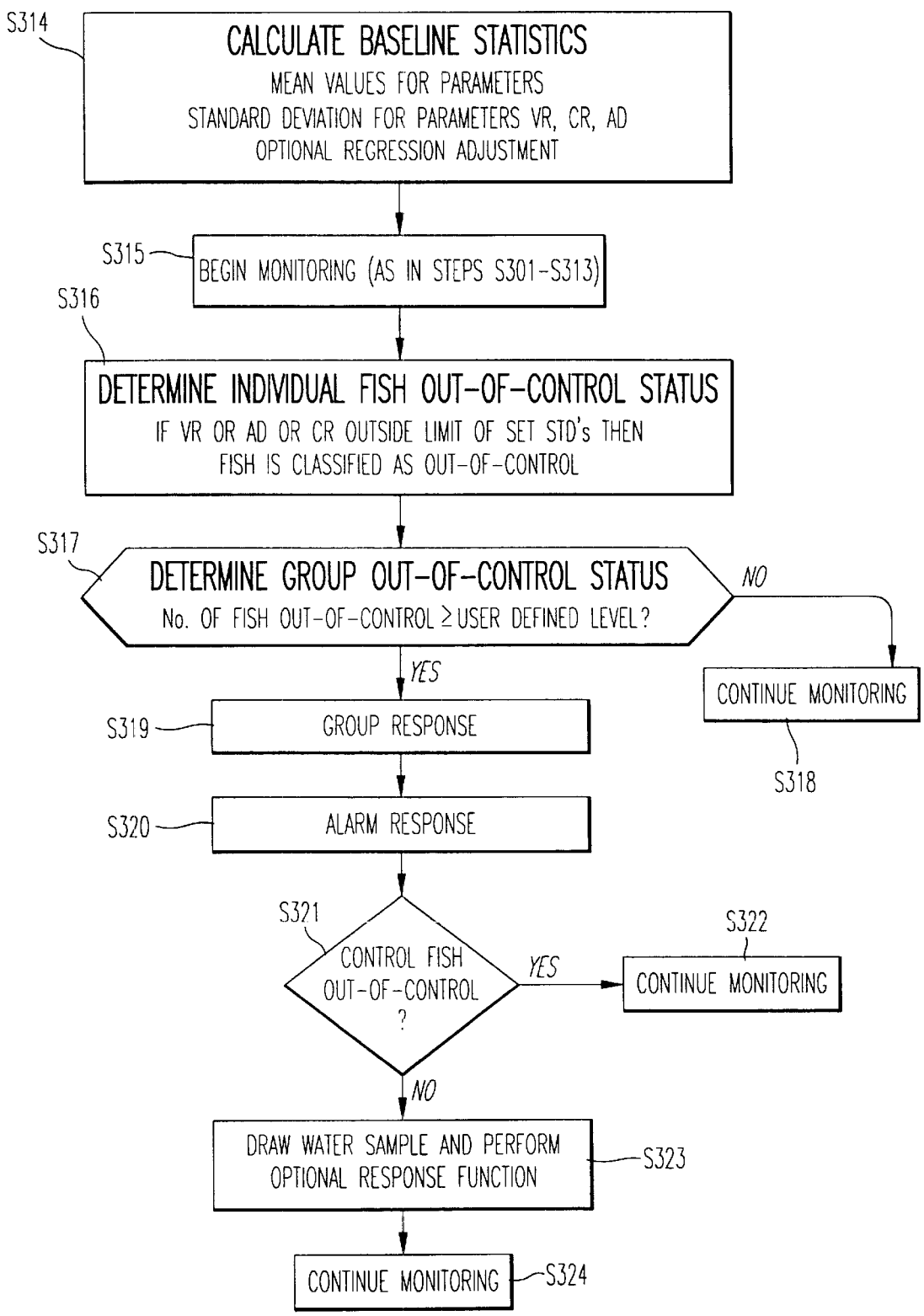
FIG. 3 is a flowchart illustrating a process for distinguishing between coughs, whole body movement, changes in ventilatory rate, and other behavior to determine when an alarm state occurs.

Turnings to FIG. 3B, further signal processing steps and functions performed by system 10 are illustrated. Step S314 calculates baseline statistics for use in determining when an out-of-control situation has occurred and when an alarm response is to be initiated by the system. The mean value and standard deviation for each of the parameters VR, CR, and AD, are calculated and stored in this step, and a Chi-square analysis is performed on percent whole body movement. An optional regression adjustment as described below may be performed in step 314 as well to adjust ventilatory parameters for changes in dissolve oxygen level and water temperature.

Step S314 may be performed over an extended period of time in which the fish 22 are exposed only to control water 27 in the absence of any contaminants or impurities that may be present in the source water 12 to be monitored. In this way, fish behavior may be characterized under "clean water" conditions for use in subsequent comparisons with the behavior of the same fish under exposure conditions. Step S314 also may be used to calculate moving averages for VR, CR, and AD. These data can be used to characterize changes in ventilatory behavior for either exposure or control fish, or both, over time.

Whole body movement (PM) is handled differently than the ventilatory parameters VR, CR, and AD as follows. When the level of whole body movement PM is greater than or equal to a value of twenty for at least fifty percent of the print interval, the corresponding fish is removed from the system and the data from that particular fish are not used in determining baseline statistics. The reason for this action is that significant amounts of ventilatory data are lost when whole body movement is so extensive, which could result in poor ventilatory parameter determination if the limited data were used in the subsequent analysis.

Step S314 also performs an optional regression adjustment on environmental variables as follows. Let Ti, Di denote the water temperature and dissolved oxygen levels respectively, at time i during the baseline study. Let Tm, Dm denote the baseline average levels of these variables. If the regression option is exercised, the regression model:

$$Xi = B0 + B1Ti + B2Di \text{ for } i=1,2,\ldots N \qquad (1)$$

is fitted by ordinary least squares where B0, B1, and B2 are the estimated regression coefficients used to adjust the test period responses to the levels Tm, Dm; and Xi is the measured ventilatory parameter at time i with corresponding water temperature Ti and dissolve oxygen level Di. The resulting regression coefficients are useful in applications of system 10 where there are significant changes in the dissolve oxygen level or temperature of the water being monitored. The same regression adjustment as illustrated here could be performed using other environmental variables such as pH and conductivity.

Step S315 performs signal monitoring and processing as described in steps S301–S313 of FIG. 3A, in which ventilatory parameters are characterized and quantified. Step S316 determines when an individual fish is out-of-control or beyond a predetermined threshold behavioral limit. If either VR or AD or CR is outside of a specified number of standard deviations from the baseline data provided by step S314, then the fish behavior is classified as out-of-control. The threshold used in step S316 may be determined based upon real-time control fish behavior as well as baseline statistics. In this way, the ventilatory parameters can be compared with either previously collected data from the baseline study of the same fish that are now exposed to the water being monitored, or with simultaneous data from control fish that are not exposed to the sample water source, or both baseline data and control fish data.

Step S317 determines whether there is a group response. If the number of fish characterized as out-of-control in step S316 is greater than or equal to a specified threshold, then a group response is identified and processing continues to step S319. If not, then monitoring is continued in step S318. The fish out-of-control threshold used in step S317, like the number of standard deviations used in step S314, will vary according to user preference as to the level of sensitivity desired for a particular application of the invention. A threshold of five standard deviations and seventy percent of the fish out-of-control have been used with successful results at the groundwater discharge treatment facility application described above. Specific values for a given application, however, may be selected after observing fish behavior during acclimation and baseline studies. Appropriate values will vary with local water conditions, the sensitivity of the organisms used for biomonitoring, and the desired sensitivity of the system. For example, where system 10 is used to monitor the status of a normally pristine water reservoir, the desired sensitivity to changes in fish ventilatory parameters would be high. One may, under such circumstances, select a threshold of one standard deviation from the mean ventilatory parameters and a fish out-of-control setting of twenty-five percent as the desired thresholds used for this particular application of system 10. If two out of eight fish, for example, are out-of-control, the system 10 would initiated an alarm response.

In step S319 a group response has been identified and an alarm response, step S320, is initiated. Step S320 may be a simple audible or visual alarm or a more elaborate automated response function. For example, step S320 can be used to warn personnel at a treatment facility or factory from which the sample water is drawn of a possible problem in water quality. Also, the discharge of water can be stopped or diverted into holding tanks automatically by step S320 in reply to a group response determination in step S319 until further analysis, corrective action, or both are taken.

Step S321 determines if control fish are out-of-control using the same criteria as used in steps S316–S317 for exposure fish. If these control fish also indicate a group response, monitoring is continued in step S322. Step S323 takes and stores a water sample from the same water source as that which caused the group response. This step also can be used to initiate further remedial action not taken in step S320. Step S324 then continues monitoring of fish ventilatory behavior.

Having provided a detailed description of the signal processing performed by the present invention, attention is now turned to the various hardware components.

The process of steps S301 through S324 described above may be performed on various types of controllers 30. The preferred embodiment uses a standard personal computer (microprocessor) to perform this function for ease of programming, versatility, and overall friendly user interface. For example, the user selected parameters discussed above (group response threshold, whole body movement threshold, sample interval duration, and the like) are conveniently presented in a screen menu with a standard PC, the operation of which is generally well known without special training in how to use the controller. In this particular embodiment, a 120 MHZ personal computer with 16 MB of RAM is used for both controller 30 and remote host 44. The interface between controller 30 and the other system components is described below with reference to FIG. 5.

Amplifier 26 may be any device capable of amplifying the signals from electrodes 24–25. In the present embodiment it is a multiple channel amplifier with a low-pass analog filter. It receives the raw input signals from electrodes 24–25 of exposure chamber 20, amplifies the signals, filters out high frequency signals beyond a certain frequency, then transmits the filtered and amplified analog signals to controller 30 via signal cables 28–29. In this particular embodiment, a 32-channel, rack mounted amplifier system from Dataforth, Inc. was selected for this function. It provides amplification by a factor of 1000, and filters out high frequency signals beyond 50 Hz so as to remove noise produced by the 60 Hz power supply. The commercially available amplifier 26 was modified with the addition of two 470-microfarad electrolytic capacitors to the front end of the amplifier system to eliminate D.C. offset created by exposure chamber 20.

Figure 4:
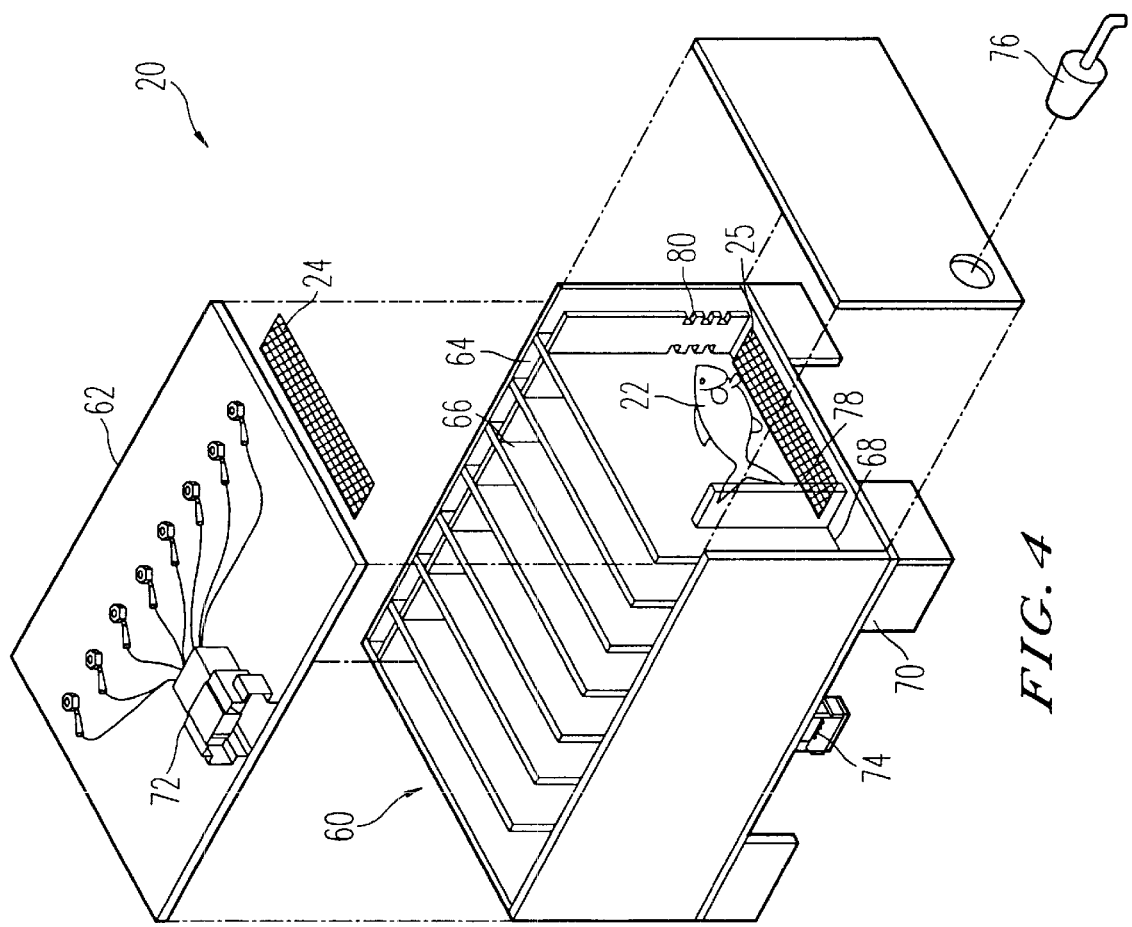
FIG. 4 is a perspective view of an exposure tank which can be used in the present invention.

Turning to FIG. 4, a perspective view of exposure chamber 20 for housing fish 22 is illustrated. Exposure chamber 20 provides a compact and convenient array of eight individual fish chambers 66, each with top electrode 24, bottom electrode 25, water input pre-chamber 64, and drain post-chamber 68. Electrodes 24–25 and wiring connections are preferably made from a corrosion resistant material. Exposure chamber top 62 includes waterproof electrical plug 72, which is connected to each of the top electrodes 24. When placed on top of base 60, top 62 covers fish chamber 66 and drain post-chamber 68 leaving water input pre-chamber 64 open to receive a water inlet supply. The walls of fish chamber 66 preferably reduce or prevent visual contact between adjoining chambers. For example, the walls may be frosted or opaque plastic as opposed to the clear plastic used for the remainder of base 60 and top 62. This helps to reduce fish stimuli that would otherwise occur with visual contact between fish in adjacent compartments. Clear plastic is preferred for the top and bottom to allow the chamber contents to be viewed from above or below.

The electrodes 24–25 may be made of a wide variety of materials. One example of a readily available, corrosion resistant material which can be used is 316 stainless steel. However, in some situations, metal electrodes may undergo galvanic interactions with water in the exposure chambers 20, particularly when the water has a high conductivity on the order of 4720 $\mu$S/cm or above (occurring, for example, with a salinity level of approximately 3 ppt), resulting in increased noise and signal instability. In such situations, it may be preferable to employ a nonmetallic material, such as graphite, for the electrodes 24–25.

Figure 7:
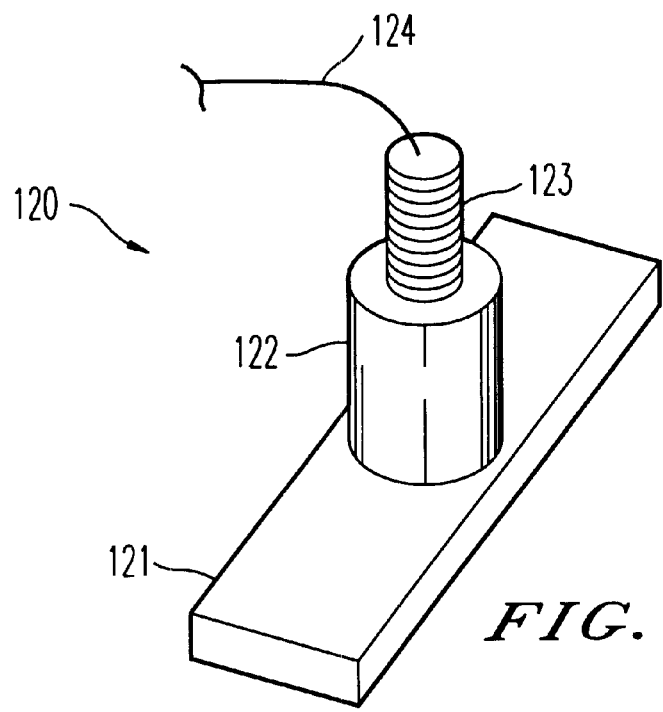
FIGS. 7 and 8 are respectively a perspective view and a vertical cross-sectional view of an example of an electrode assembly.
Figure 8:
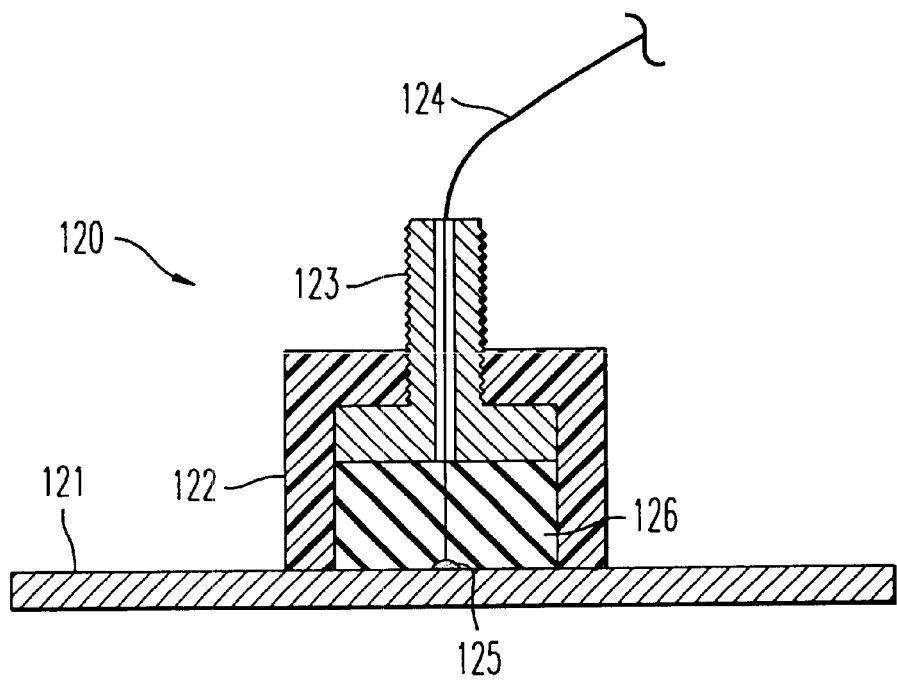

FIGS. 7 and 8 are respectively a top perspective view and a vertical cross-sectional view of an example of an electrode assembly 120 which can be used as one or both electrodes 24–25. The illustrated assembly 120 includes an electrically conducting electrode plate 121, a spacer 122 for positioning the plate 121 with respect to the interior of an exposure chamber 20, and a bolt 123 for securing the assembly 120 to the exposure chamber 20. The illustrated plate 121 is an elongated rectangular strip of graphite with a width of 0.8 inches and a length of 3.5 inches, although the dimensions of the plate 121 are not critical. The spacer 122, which is made of acrylic or other electrically insulating material, is secured to the plate 121 by any convenient manner, such as by bonding. It has a central bore for receiving the bolt 123, which in this example is made of nylon or other electrically insulating material. The bolt 123 has a central bore through which can pass a lead wire 124 which is electrically connected to the plate 121 in any manner which assures good electrical conductivity, such as by using a conductive bonding material 125 of silver epoxy or other suitable material. The interior of the spacer 122 between the head of the bolt 123 and the plate 121 may be filled with a nonconductive epoxy 126 or other nonconductive material in order to make the interior of the spacer 122 watertight and to increase the structural stability of the connection between the lead wire 124 and the plate 121. The threads of the bolt 123 which extend outside of the spacer 122 may be passed through a corresponding opening in the exposure chamber 20 and affixed with a nut on the exterior of the exposure chamber 20 to secure the electrode assembly 120 in place. Each spacer 122 is sufficiently long that at least one face of the corresponding plate 121 is immersed in the water in the exposure chamber 20. The lead wire 124 can be connected to the plug 72 so that the output signals from the assembly 120 can be supplied to external equipment.

Base 60 includes a waterproof electrical plug 74, which is electrically connected to each of the bottom electrodes 25. Base 60 further includes legs 70 and drain 76. When in use with the present invention, water flows into exposure chamber 20 through water inlet chambers 64 where it enters fish chambers 66 through holes 80. Water flows out of fish chambers 66 by flowing over overflow dividers 78 and into drain chamber 68. This flow path from low inlet to high outlet provides increased water mixing and reduced stratification within fish chamber 66 to ensure that all fish 22 are exposed to the same water conditions and water quality. After leaving fish chamber 66, water flows into drain post-chamber 68, which serves as a common reservoir for drain water from all eight fish chambers 66. Water flows out of post-chamber 68 via drain 76.

In addition to providing inlet water mixing and reduced stratification within fish chamber 66, exposure chamber 20 provides a compact and convenient array of eight fish chambers that can be installed, removed, and inspected with minimal effort. The top-bottom electrode arrangement of chamber 20 provides for improved detection of ventilatory responses as compared to a front-back arrangement. Normally a fish in such a tank will orientate its head upstream towards the front panel of the tank, but will occasionally change its position and orientation in the tank. A front-back electrode arrangement can cause signal alteration due to changes in fish position and orientation relative to the electrodes, but a top-bottom arrangement is much less affected by such changes.

While a preferred embodiment of an exposure chamber 20 has been described and illustrated, various modifications and variations are possible. For example, the number of individual fish chambers 66 per exposure chamber 62 could vary and the pre-chamber 64 and post-chamber 68 could be modified while still providing uniform mixing of the water prior to organism exposure, and reduced water stratification within the chamber as taught above.

Figure 5:
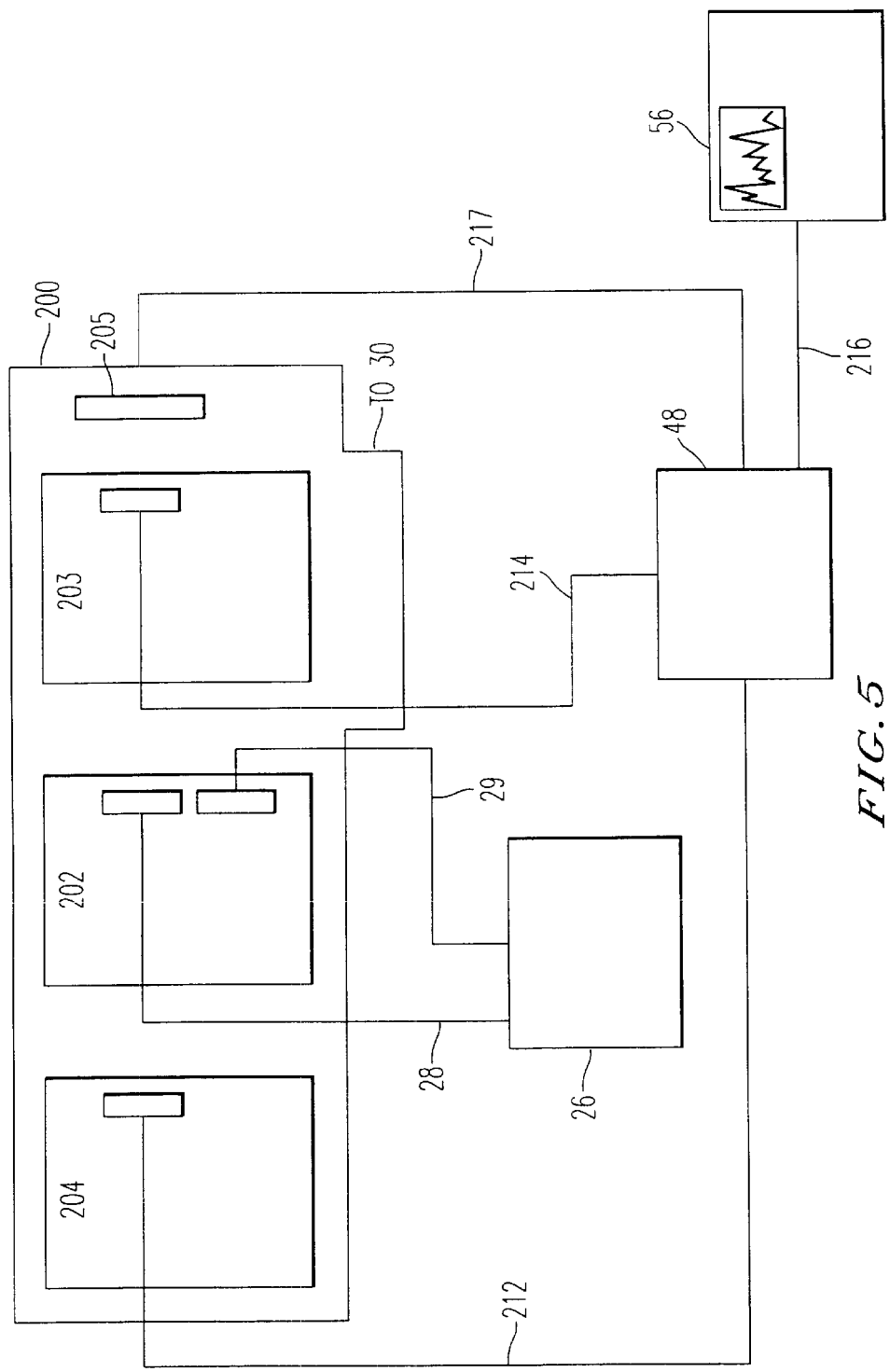
FIG. 5 is a schematic of an internal carrier board which can be used in the present invention for integration with a standard microprocessor.

Turning to FIG. 5, a schematic of an internal carrier board 200 is illustrated for integrating the present invention with a standard PC as controller 30. Carrier board 200 is a data acquisition board that interfaces directly with the internal bus of ISA and EISA computers, and may be plugged directly into a PC motherboard to provide integration of controller 30 with other components of system 10. Carrier board 200 includes expander/sequencer module 202, output module 203, and input module 204.

The ventilatory signals from amplifier 26 are provided as analog input data to module 202 via signal cables 28–29. These analog ventilatory signals are provided to input module 204 via a daisy chain (internal bus) between modules 202 and 204. Input module 204 receives analog ventilatory signals from module 202, amplifies the signals by a factor of ten and performs an analog-to-digital conversion of the data signals, which are then read by controller 30 and analyzed as described above. These ventilatory data signals also are written by controller 30 to output module 203, which performs a digital-to-analog conversion, and transmits the resulting ventilatory signals to termination panel 48 via cable 214. The analog ventilatory data signals at terminal panel 48 may be viewed on oscilloscope 56, which is connected to termination panel 48 via cable 216.

Module 204 may also receive analog input signals from termination panel 48 via cable 212. This feature is used to provide controller 30 with information from an external source such as a water treatment facility. For example, when the facility is discharging effluent water, a signal may be sent from the treatment facility control room to system 10 indicating that a discharge has occurred. This information would be provided to controller 30 via termination panel 48, cable 212, and input module 204. The analog signals received by input module 204 are converted to digital form and transferred to controller 30.

Internal carrier 200 further includes a digital output port 205 to send digital control signals to termination panel 48 via cable 217. Digital output port 205 is used in this example embodiment to control solenoid valve 52, water sampler 54, and control signal 58 as described with reference to FIG. 6 below.

The internal carrier board 200 may itself be, or may be assembled from, off-the-self components. In this particular embodiment, internal carrier board 200 is a model PCI-20041C-2A. Module 202 is an analog expander/sequencer option module, model PCI-20031M-1. Output module 203 is a 12-bit analog output module, model PCI-20003M-2. And input module 204 is a 12-bit analog input module, model PCI-20002M-1, all of which are conmmercially available from Intelligent Instrumentation, Inc.

Figure 6:
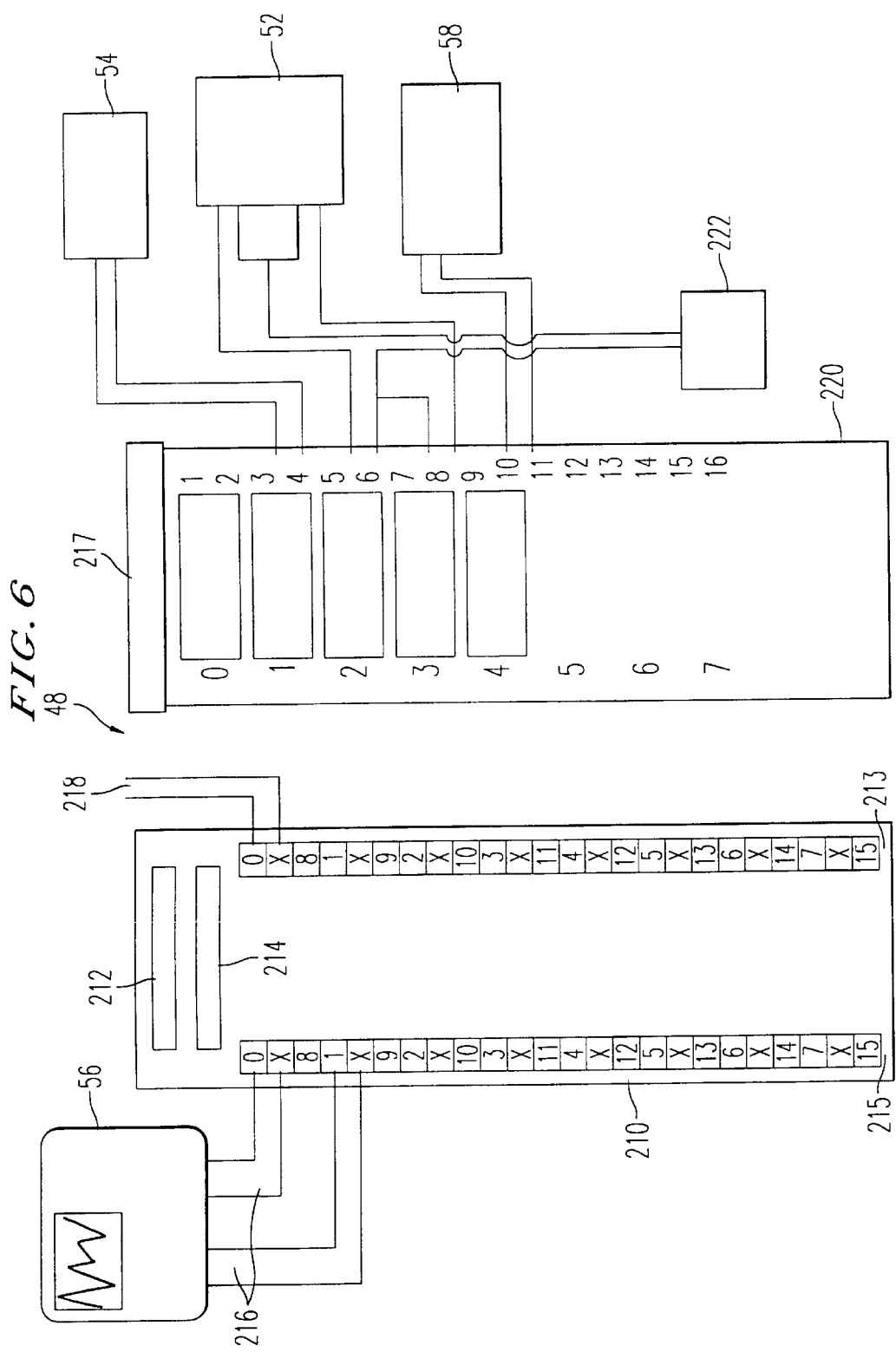
FIG. 6 is a schematic of a termination panel used as an interface between a microprocessor and other components of the present invention.

Turning to FIG. 6, a schematic of a termination panel 48 is illustrated. Termination panel 48 includes signal module 210 and control module 220. Signal module 210 receives analog input from module 203 of internal carrier 200 via cable 214. Module 210 includes analog input terminal strip 213 and analog output terminal strip 215. Channel 0 and 1 of output terminal 214 are used in this illustration to provide an analog voltage signal to oscilloscope 56 via cable 216. Channel 0 of input terminal 213 receives signal 218 from an external source indicating, for example, that a wastewater or effluent discharge is taking place. Additional terminals for further input data and output functions are provided for expansion as may be desired for a particular application of the invention. More information from a water treatment facility, for example, may be provided and analyzed by controller 30 via the unused channels available on input terminal 213. Similarly, additional output information could be provided to remote sites, monitoring stations, and the like using the unused channels of output terminal 215.

The function of terminal panel 48 may be divided among a number of separate devices, perhaps even eliminating the need for this particular component of system 10. It is used in this embodiment to separate power supply 222 and other component wiring from controller 30 and amplifier 26, thus avoiding possible signal noise that could result from a clustering of components.

Termination panel 48 also includes control module 220 for controlling certain component functions based upon a digital signal from controller 30. Control signals are received from controller 30 via digital output module 205 and cable 217. A 120-volt AC power supply 222 is provided to module 220 for use in opening or closing water control valves, sounding alarms, and similar functions. In this embodiment, module 220 provides output control of solenoid valve controller 52, water sampler 54, and control signal 58. Solenoid valve controller 52, in response to a signal from controller 10 via termination panel 48, provides water to sensor 40 for sensing water characteristics from either source 12 via stream 17 or control water source 27. In this way, sensor 40 can be calibrated automatically by controller 30 using the known water characteristics of control water source 27. Sensor 40 is a commercially available water quality analyzer such as the H20 multiprobe available from by Hydrolab, Inc.

Control signal 58 may be used to energize a simple audible alarm and lamp to warn of a water quality problem, or it may be a previously established response procedure to automatically isolate or correct the cause of the problem. The latter is accomplished for a given application of the invention with the assistance of local facility engineers using standard equipment and procedures. For example, corrective action at a particular water treatment facility may call for additional holding time in a reaction vessel, aeration pond, or the like before the water is discharged to the environment. In the case where system 10 is used to monitor a source 12 of drinking water before it enters a potable water system, automated corrective action may call for immediate isolation of water source 12 to prevent it from entering the potable water system until the water quality problem has been resolved. As illustrated in the above discussion, system 10 provides a general-purpose automated biomonitoring system for use in monitoring the water quality of any source of water, and is readily integrated with other control systems or data monitoring devices.

Attention is now turned to variations in the conductivity of the water to be monitored. An increase in the conductivity C of the water in an exposure chamber 20 causes a decrease in the measurable amplitude of a fish ventilation signal captured by the electrodes 24–25 in the chamber 20. The effect of conductivity on the measurable amplitude can cause a number of problems. One problem is that the amplitude of the signal received by the electrodes 24–25 may fall below a measurable limit. Another problem is that variations in the conductivity cause amplitude changes in the signal received by the electrodes 24–25 that are not directly caused by the fish being monitored, producing misleading results unrelated to actual changes in water quality. It is therefore desirable to be able to adjust the amplitude of a fish ventilation signal captured by the electrodes 24–25 to compensate for variations in water conductivity C.

To investigate the relationship between the actual amplitude V0 of a signal generated by a fish, the measured amplitude V1 of the ventilation signal captured by the electrodes 24 and 25, and water conductivity C, a pair of test electrodes were placed in an exposure chamber 20 at a location between electrodes 24 and 25. A pulsating DC voltage V0 comparable in amplitude and frequency with those of a signal generated by an actual fish was applied to the test electrodes, and the amplitude V1 of the signal captured by electrodes 24 and 25 was measured over a range of conductivities C. Regression analysis of the test data thus obtained was then employed to calculate a function f(V0,C) which approximated V1 as a function of V0 and C. The test data could be modeled by a variety of functions (such as exponential functions, logarithmic functions, polynomial functions, and linear functions), but a function f of the form $$V1 = f(V0, C) = k \cdot V0 \cdot C^{-x} \quad (2)$$

gave a particularly good fit over a wide range of conductivities, wherein k is a constant and 0<x<1. The exponent x may have a constant value for all conductivities, but a better fit to the data may be obtained if x varies with the conductivity. For example, for the exposure chamber 20 and the electrodes 24–25 employed to perform the testing, a value for x of approximately 0.57 gave the best fit when C was in the range of 3070–4690 μS/cm, and a value of approximately 0.71 gave the best fit when C was in the range of 9150 to 34,000 μS/cm. The constant k depends upon the configuration of the electrodes 24–25 and the exposure chamber 20.

If the amplitude V1 of the signal captured by electrodes 24–25 and the conductivity C are known, the amplitude V0 of the signal generated by a fish can be calculated using the inverse $f^{-1}$ of f, i.e., by the formula $$V0 = f^{-1}(V1, C) = (V1 \cdot C^x)/k \quad (3)$$

If the signal from the electrodes 24–25 having an amplitude V1 is replaced by a corrected signal having an amplitude V2 given by the formula $$\begin{aligned} V2 &= a \cdot f^{-1}(V1, C) + b \\ &= a \cdot V1 \cdot C^x / k + b \end{aligned} \quad (4)$$

wherein a and b are constants, the corrected signal will have an amplitude V2 which is independent of C. The constants a and b can be selected so that V2 will be suitable for the requirements of amplifier 26, controller 30, or other equipment which is to process the corrected signal. If a=1 and b=0, then V2=V0.

Using formula (4), the embodiment of FIG. 1 may be modified to perform signal correction of the signal from the electrodes 24–25 so that the signal received by the controller 30 will have an amplitude which is independent of variations in conductivity C. Signal correction can be implemented in a variety of ways. For example, it can be carried out by analog signal processing circuitry, by digital signal processing circuitry, or by software. A device for performing signal correction can be installed in various locations, such as within amplifier 26, between electrodes 24–25 and amplifier 26, between amplifier 26 and controller 30, or within controller 30.

Figure 9:
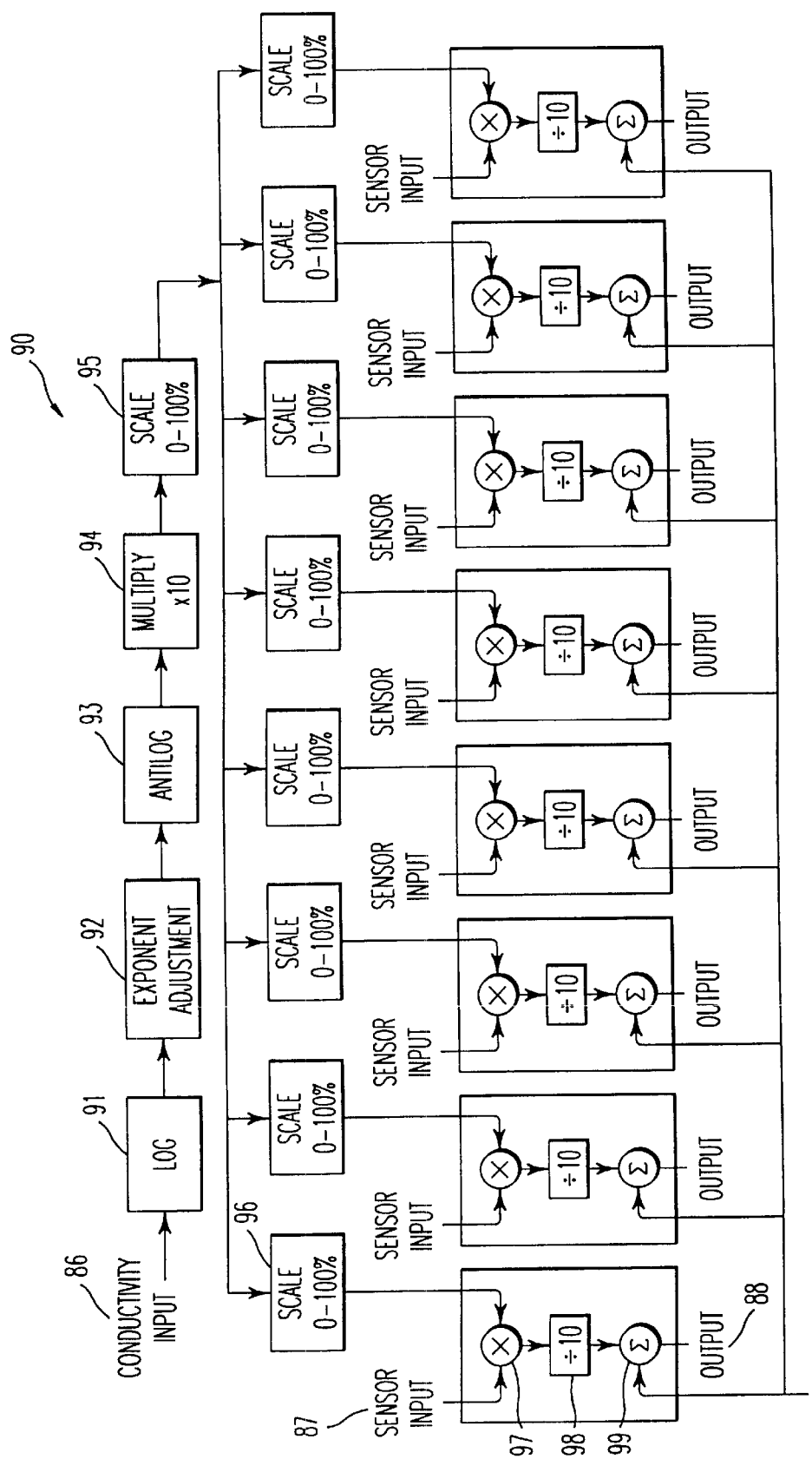
FIG. 9 is a block diagram of an example of a signal correction circuit for correcting a ventilation signal for water conductivity.

FIG. 9 is a block diagram of an example of an analog signal processing circuit 90 which can be used to correct the ventilation signal from electrodes 24–25 to compensate for conductivity C according to formula (4). This circuit 90 is intended to be installed between amplifier 26 and controller 30 of FIG. 1, but it can instead be installed in other locations. An analog conductivity signal 86 from water quality sensor 40 which is proportional to conductivity C is first input to a logarithmic amplifier 91 which generates a signal proportional to a logarithm of the conductivity signal 86. The output of logarithmic amplifier 91 is provided to an amplifier 92, which multiplies the input signal by a value corresponding to the exponent x to which the conductivity C is to be raised in formula (4). The value may be constant, or it may be one which varies in accordance with the conductivity C, as described above. The output of amplifier 92 is provided to an antilogarithm generator 93, which generates an output signal proportional to the antilogarithm of the input signal. The output signal of antilogarithm generator 93 is thus proportional to $C^x$ in formula (4). The output from antilogarithm generator 93 is then input to an amplifier 94, which multiplies the input signal by ten or other predetermined value, and the amplified signal is then input to another amplifier 95, which multiplies the input signal by a value between 0 and 1 to perform scaling. The output of amplifier 95 is then input to a separate amplifier 96 for each output channel of amplifier 26 of FIG. 1. By way of example, FIG. 9 shows eight amplifiers 96 for eight output channels from amplifier 26, each output channel carrying an amplified ventilation signal for a different fish chamber 66 in exposure chamber 20. In each amplifier 96, the output signal from amplifier 95 is multiplied by a value between 0 and 1. The gains of these amplifiers 96 may be adjusted independently of each other. Amplifier 95 permits fine tuning of the output signals for an entire bank of fish chambers 66 in an exposure chamber 20, while amplifiers 96 permit fine tuning of the output signals for individual fish chambers 66. Various of these amplifiers 94–96 can be combined with each other or omitted. For example, the functions of amplifiers 94 and 95 can be incorporated into each of amplifiers 96, or amplifiers 94 and 95 can be combined to form a single amplifier, or amplifiers 96 can be omitted if independent control of individual output channels of amplifier 26 is unneeded.

The output of each amplifier 96 is supplied to a corresponding multiplying amplifier 97, in which it is multiplied by an input signal 87 (proportional to V1 in formula (4)) provided by one channel of amplifier 26. The output of each amplifier 97 may then be applied to a scaling amplifier 98 which reduces the input signal, if necessary, according to the requirements of the system. The output of the scaling amplifier 98 corresponds to the term $a \cdot V1 \cdot C^x/k$ in formula (4). The output of each scaling amplifier 98 is then input to a corresponding adder 99, which combines the signal from the scaling amplifier 98 with a constant voltage 89 corresponding to constant b in formula (4). The output 88 of each adder 99 (corresponding to V2 in formula (4)) is then provided to controller 30 of FIG. 1 for evaluation in the manner described above with respect to FIGS. 2, 3a, and 3b.

All of the components in the signal processing circuit 90 of FIG. 9 may be conventional and are either available as off the shelf components or can be easily constructed by those of ordinary skill in the electronic arts based on well-known designs for analog circuitry. The same applies for digital or software implementations of the functions of this circuit 90.

As a result of this circuit 90, determinations of ventilatory responses of fish in exposure chambers 20 can be performed accurately, regardless of variations in conductivity C in the exposure chambers 20.

The circuitry shown in FIG. 9 is designed for use when the function f(V0,C) has the value given by formula (2). If it is desired to use a different type of function f, such as an exponential function, a logarithmic function, a polynomial function, or a linear function, the circuitry may be readily modified by one skilled in the art to calculate the corresponding value of $f^{-1}$.

The foregoing description of specific embodiments of the present invention have been presented for purposes of illustration and description. They are not intended to be exhaustive or to limit the invention to the precise forms disclosed, and many modifications and variations are possible in light of the above teaching. The embodiments illustrated and described above were chosen to best explain the principles of the invention and its practical application, thereby enabling others skilled in the art to best utilize the invention and various embodiments with various modifications as are suited to the particular use contemplated. It is intended that the scope of the invention be defined by the following Claims and their equivalents.

We claim:

1. An apparatus for monitoring and evaluating water quality using ventilatory behavior and body movement of an aquatic organism, comprising:

an exposure chamber for housing an aquatic organism;

an electrode capturing a signal from the aquatic organism indicative of ventilatory behavior and body movement of the aquatic organism;

a sensor which measures conductivity C of water in the exposure chamber;

signal correcting means responsive to the sensor and the electrode for generating a corrected signal which corrects the signal captured by the electrode in accordance with the conductivity C measured by the sensor; and a controller which determines, based on the corrected signal, when a ventilatory parameter of the aquatic organism exceeds a threshold.

2. An apparatus as recited in claim 1 wherein a ratio V2/V1 of an amplitude V2 of the corrected signal to an amplitude V1 of the signal captured by the electrode increases as the conductivity C measured by the sensor increases.

3. An apparatus as recited in claim 2 wherein the ratio increases nonlinearly as the conductivity C measured by the sensor increases.

4. An apparatus as recited in claim 1 wherein the signal correcting means generates the corrected signal with an amplitude V2 given by the formula $$V2 = a \cdot V1 \cdot C^x/k + b$$

wherein V1 is an amplitude of the captured signal, a, b, and k are constants, and $0 < x < 1$.

5. An apparatus as recited in claim 4 wherein x increases as the conductivity C increases.

6. An apparatus as claimed in claim 1 wherein the correcting means comprises an analog signal processing circuit.

7. A method of evaluating water quality comprising:

capturing with an electrode a signal generated by an aquatic organism disposed in water to be evaluated and indicative of ventilatory behavior and body movement of the aquatic organism;

measuring conductivity C of the water;

generating a corrected signal which corrects the captured signal in accordance with the measured conductivity C; and determining based on the corrected signal when a ventilatory parameter of the aquatic organism exceeds a threshold.

8. A method as recited in claim 7 including increasing a ratio V2/V1 of an amplitude V2 of the corrected signal to an amplitude V1 of the captured signal as the conductivity C measured by the sensor increases.

9. A method as recited in claim 8 including nonlinearly increasing the ratio as the measured conductivity C increases.

10. A method as recited in claim 7 including generating the corrected signal with an amplitude V2 given by the formula $$V2 = a \cdot V1 \cdot C^x/k + b$$

wherein V1 is an amplitude of the captured signal, a, b, and k are constants, and $0 < x < 1$.

11. A method as recited in claim 10 including increasing x as the conductivity C increases.

12. A method as recited in claim 7 including generating a test voltage V0 at various values of C, measuring the amplitude V1 of a signal resulting from the test voltage V0 and captured by the electrodes, deriving a function f(V0, C)=V1 by regression analysis of V0, V1, and C, and generating the corrected signal with an amplitude V2 given by the formula $$V2 = a \cdot f^{-1}(V1,C) + b$$

wherein a and b constants, and $f^{-1}(V1,C) = V0$ is the inverse of the function f(V0,C).

* * * * *